United States Patent
Hirai et al.

(10) Patent No.: US 6,202,032 B1
(45) Date of Patent: Mar. 13, 2001

(54) METHOD FOR FORMING A CALIBRATION LINE IN AN INFRARED GAS ANALYZER

(75) Inventors: Hitoshi Hirai; Masahiko Sannomiya, both of Miyanohigashi-machi (JP)

(73) Assignee: Horrba, Ltd., Kyoto (JP)

( * ) Notice: Subject to any disclaimer, the term of this patent is extended or adjusted under 35 U.S.C. 154(b) by 0 days.

(21) Appl. No.: 09/244,307

(22) Filed: Feb. 4, 1999

(30) Foreign Application Priority Data

Apr. 18, 1998 (JP) .................................................. 10-124220

(51) Int. Cl.[7] .............................. G01N 21/00; G01L 27/00
(52) U.S. Cl. .............................. 702/100; 702/90; 73/1.02; 73/1.06; 250/339.12
(58) Field of Search ..................................... 702/100, 101, 702/90; 73/1.02–1.03, 1.06, 1.07; 250/288, 343, 345, 339.12

(56) References Cited

U.S. PATENT DOCUMENTS

| 3,957,372 | * | 5/1976 | Jowett et al. | .................... 250/345 |
| 4,499,378 | * | 2/1985 | Miyatake et al. | .................... 250/343 |
| 5,804,695 | * | 9/1998 | Dageforde | ............................ 73/1.07 |
| 6,000,275 | * | 12/1999 | Nishina et al. | ........................ 73/1.05 |

* cited by examiner

*Primary Examiner*—Marc S. Hoff
*Assistant Examiner*—Bryan Bui
(74) *Attorney, Agent, or Firm*—Oppenheimer Wolff & Donnelly LLP

(57) ABSTRACT

A forming method for a calibration curve in an infrared gas analyzer. The forming method minimizes the systematic error that occurs in the infrared gas analyzer improves measuring precision. The forming method modifies a method in which gases having different concentrations are supplied to an infrared gas analyzer. The gas analyzer has the outputs corresponding to the gas concentrations, and samples the gas concentrations as a plurality of points, the number of which is not less than four. A calibration curve is approximated by up to a fourth-order polynomial using a method of least squares based upon the measured values of not less than 4 points thus sampled. In carrying out the above-mentioned polynomial approximation, an inverse number of the square of the divided ratio at each point of the calibration curve is used so as to carry out a weighting operation.

1 Claim, 4 Drawing Sheets

METHOD FOR FORMING A CALIBRATION LINE IN AN INFRARED GAS ANALYZER

BACKGROUND OF THE INVENTION

1. Field of the Invention

This invention relates to a method for forming a calibration curve in an infrared gas analyzer for measuring the concentration of a sample gas, such as CO and $CO_2$.

2. Description of the Prior Art

In concentration measurements for CO and $CO_2$ contained in, for example, vehicle emission gases, non-distribution type infrared gas analyzers (NDIR) are used. Along with recent rapid developments of low-emission engines, there are ever-increasing demands for high-precision infrared gas analyzers.

One of the important factors in achieving analytical precision for the infrared gas analyzer is to properly create and maintain the calibration curve. The formation of this calibration curve has been generally carried out by using a system as shown in FIG. 3. In FIG. 3, reference number 1 represents a gas analyzing section which is constituted by, for example, an infrared gas analyzer 2 for measuring gases such as $CO_2$, a preamplifier 3 for appropriately waveform-shaping the output of the infrared gas analyzer 2, and an AD converter 4 for A/D converting the output of the infrared gas analyzer that is inputted thereto through the preamplifier 3.

Reference numeral 5 represents a gas divider for generating some calibration gas SG having a known concentration and for supplying gas SG to the above-mentioned gas analyzer 1. This is arranged so that a component gas (span gas) CG of which the concentration is preliminarily determined and a dilute gas (for example, nitrogen gas or air) DG which dilutes the component gas to a predetermined concentration are given as inputs, and the generated gas SG is outputted therefrom.

Reference numeral 6 is an Main Control Unit (MCU) for supervising and controlling the entire system, which MCU is constituted by a computer. The MCU 6 controls the gas analyzing section 1 and the gas divider 5 through interface controllers (IFC) 7 and 8, and also has a computing function for carrying out concentration calculations based upon the output from the gas analyzer 1. Reference numeral 9 is a display device, for example, a touch panel display, connected to the MCU 6. Moreover, reference numeral 10 is a storage medium, for example, a hard disk, etc., which stores measured data and is provided with a plurality of files containing data to be displayed on the device 9.

In the above-mentioned arrangement, the calibration-use component gas CG and the dilute gas DG are supplied to the gas divider 5, and the component gas SG having an appropriate concentration is obtained. Then, the component gas SG, adjusted to the appropriate concentration, is supplied to the infrared gas analyzer 2 in the gas analyzing section 1, and output signals (measured values) from the infrared gas analyzer 2 are obtained as a plurality of points (not less than four as measured points). Then, these are inputted to the MCU 6 so that, based upon not less than four measured values thus obtained, the calibration curve is approximated by a polynomial not greater than its 4th order by using the method of least squares In other words, the calibration curve f(x) is represented as follows:

$$f(x)=a_0+a_1x+a_2x^2+a_3x^3+a_4x^4,$$

Assuming that the measured value is $(x_i, y_i)$, coefficients, $a_0$ through $a_4$ are obtained from the following equations:

$$\Delta \epsilon_i^2 = \{y_i-(a_0+a_1x_i+a_2x_i^2+a_3x_i^3+a_4x_i^4)\}^2 \quad (1)$$

$$\delta \Sigma \epsilon_i^2 / \partial aj = 0 (j=0-4) \quad (2)$$

Here, it is well known in the art that the principle of measurement of the infrared gas analyzer 2 follows the Lambert-Beer's law as shown in the following equation (3).

$$I=I_0 \exp(-\mu cL) \quad (3)$$

where $I_0$: intensity of incident light, I: intensity of transmitted light, $\mu$: absorption coefficient, c: concentration of a sample gas to be measured, L: thickness of gas layer.

The above-mentioned equation (3) indicates that the transmittance, which is the rate of change in the intensity of transmitted light, can be approximated to a first-order equation in a low-density area, and that as the concentration increases, it can be explicated to a higher order equation.

For example, in the exhaust-gas measurements of vehicles, it is necessary to approximate the calibration curve used in the infrared gas analyzer 2 by using a polynomial not greater than its 4th order; and in the case when the measuring range is wide, that is, in the case of a combined area of the area that can be approximated by a first-order equation and the area that can be approximated by a higher order (2nd, 3rd, 4th) equation, the precision of the calibration curve in the area that can be approximated by a first-order equation tends to deteriorate with systematic error.

FIG. 4 explains the precision of the above-mentioned calibration curve, and in FIG. 4, curve 41, indicated by a solid line, is a calibration curve, and a curve indicated by a phantom line indicates the concentration obtained by actual measurements. Moreover, symbol I is an area that can be approximated by a first-order equation, and II is an area that can be approximated by a high order (2nd, 3rd, 4th) equation. As shown in FIG. 4, the calibration curve 41 is approximately coincident with the measurement curve 42 within the area 41 that can be approximated by a higher order equation, which corresponds to a high concentration area; however, in the first-order-equation approximation area which corresponds to a low-concentration area, it deviates from the curve to a great degree, with the result that the precision of the calibration curve is lowered and $E_{rr}$% (error %) in the low-concentration area sometimes fails to meet standard criteria (±2.0% PT). Here, % PT refers to the error in reading a value. The error with the calibration curve 41 with respect to the measurement curve 42 in the above-mentioned infrared gas analyzer is classified as the system error that inevitably occurs in the measuring principle of the infrared gas analyzer.

SUMMARY OF THE INVENTION

The present invention has been devised to solve the above-mentioned problems, and its objective is to minimize the systematic error that inevitably occurs in the measuring principle of the infrared gas analyzer, and consequently to provide a forming method (hereinafter, referred to simply as a forming method for the calibration curve) for the calibration curve in the infrared gas analyzer capable of improving the measuring precision.

In order to solve the above-mentioned objective, the present invention, which relates to a method in which gases having different concentrations are supplied to an infrared gas analyzer and the outputs corresponding to the gas concentrations in this case are sampled as a plurality of points the number of which is not less than four, and in which the calibration curve isapproximated by a fourth-order polynomial using the method of least squares based upon the measured values of not less than 4 thus sampled, is characterized in that upon carrying out the above-mentioned polynomial approximation, an inverse number of the square of a divided ration at each of the calibration curve forming data is used so as to carry out a weighting operation.

The calibration curve that is obtained by the conventional forming method for the calibration curve has had a greater error in the low-concentration area; however, the forming method for the calibration curve of the present invention carries out a great weighting operation in the low-concentration area so that the error in the low-concentration area is compressed to such a degree as not to cause any problem. Moreover, even the calibration curve obtained by the conventional forming method for the calibration curve does not cause a great error in the high-concentration area, and the forming method for the calibration curve in the present invention does not carry out so great a weighting operation; thus, errors hardly occur in this area. In other words, in accordance with the forming method for the calibration curve of the present invention, it becomes possible to reduce errors in the low-concentration and high-concentration areas minimum.

DETAILED DESCRIPTION OF THE PREFERRED EMBODIMENTS

Referring to Figures, the following description will discuss an exemplary embodiment of the present invention. In the present invention, upon forming the calibration curve in an infrared gas analyzer, the following equation (4) is adopted instead of the conventional equation (1) discussed above.

$$\Delta\epsilon_i^2 = w_i \{y_i - (a_0 + a_1 x_i + a_2 x_i^2 + a_3 x_i^3 + a_4 x_i^4)\}^2 \quad (4)$$

where $w_i = 1/n^2$ (n: divided ratio).

In other words, the right side of the above-mentioned equation (1) is multiplied by an inverse number of the square of the divided ratio n, wherein $w_i$ is the weighting coefficient, and the divided ratio is CG/DG which denotes a dilution percentage.

Figure 4:
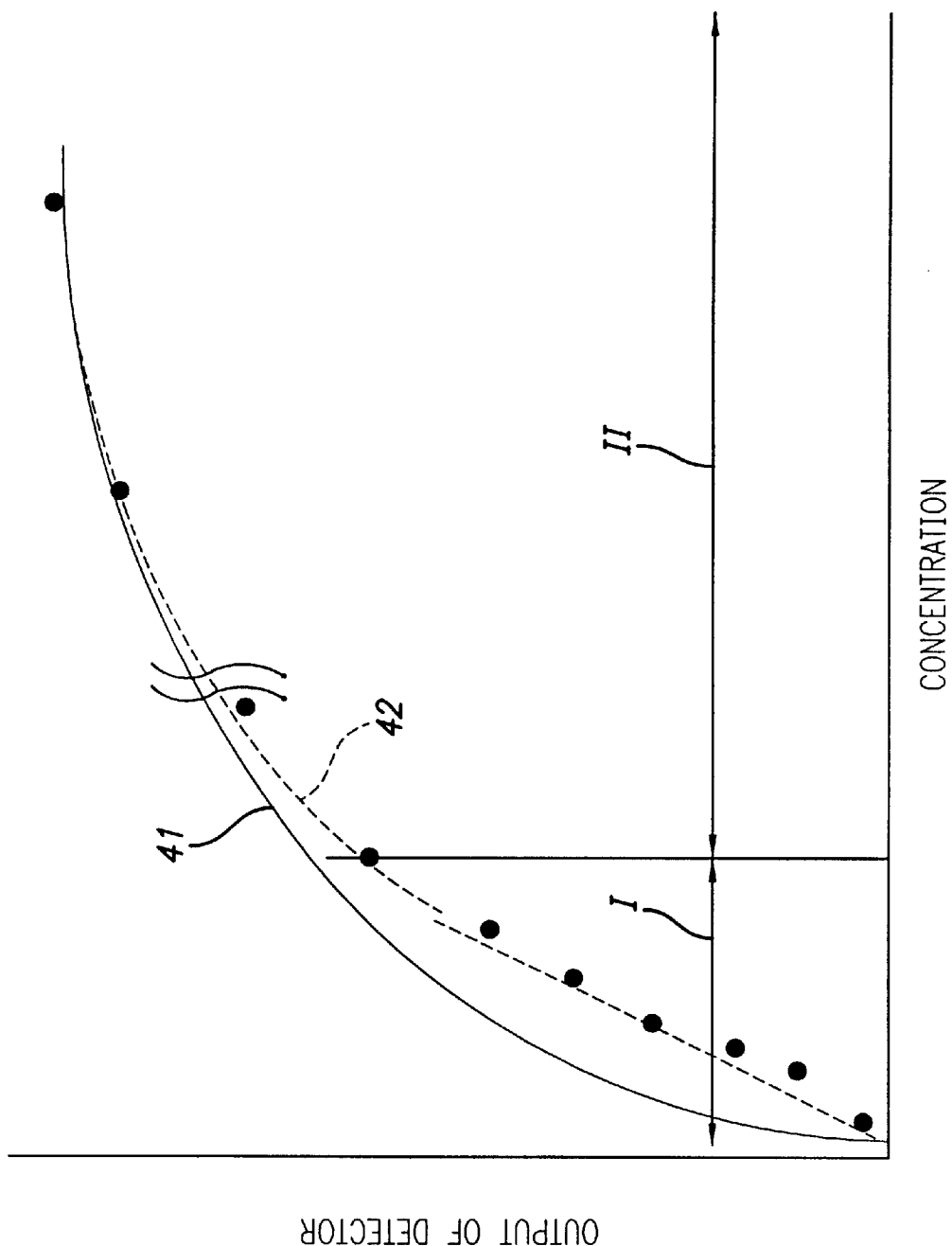
FIG. 4 is a graph explaining problems with conventional forming methods for the calibration curve.

The fact that the inverse number of the square of the divided ratio n can be effectively applied at the time of curve fitting has been found through the following processes: In the conventional calibration curve, the curve fitting is carried out by using equation (1); therefore, as shown in FIG. 4, the calibration line shows greater error as compared with the actual measurement in the low-concentration area. In order to reduce this error, a method for applying any weighting operation to the right side of equation (1) is proposed.

In such a case, three kinds of weighting operations, that is, ① an inverse number of the divided ratio, ② an inverse number of the square of the divided ratio and ③ an inverse number of the divided ratio raised to the 3rd power, are proposed.

Figure 1:
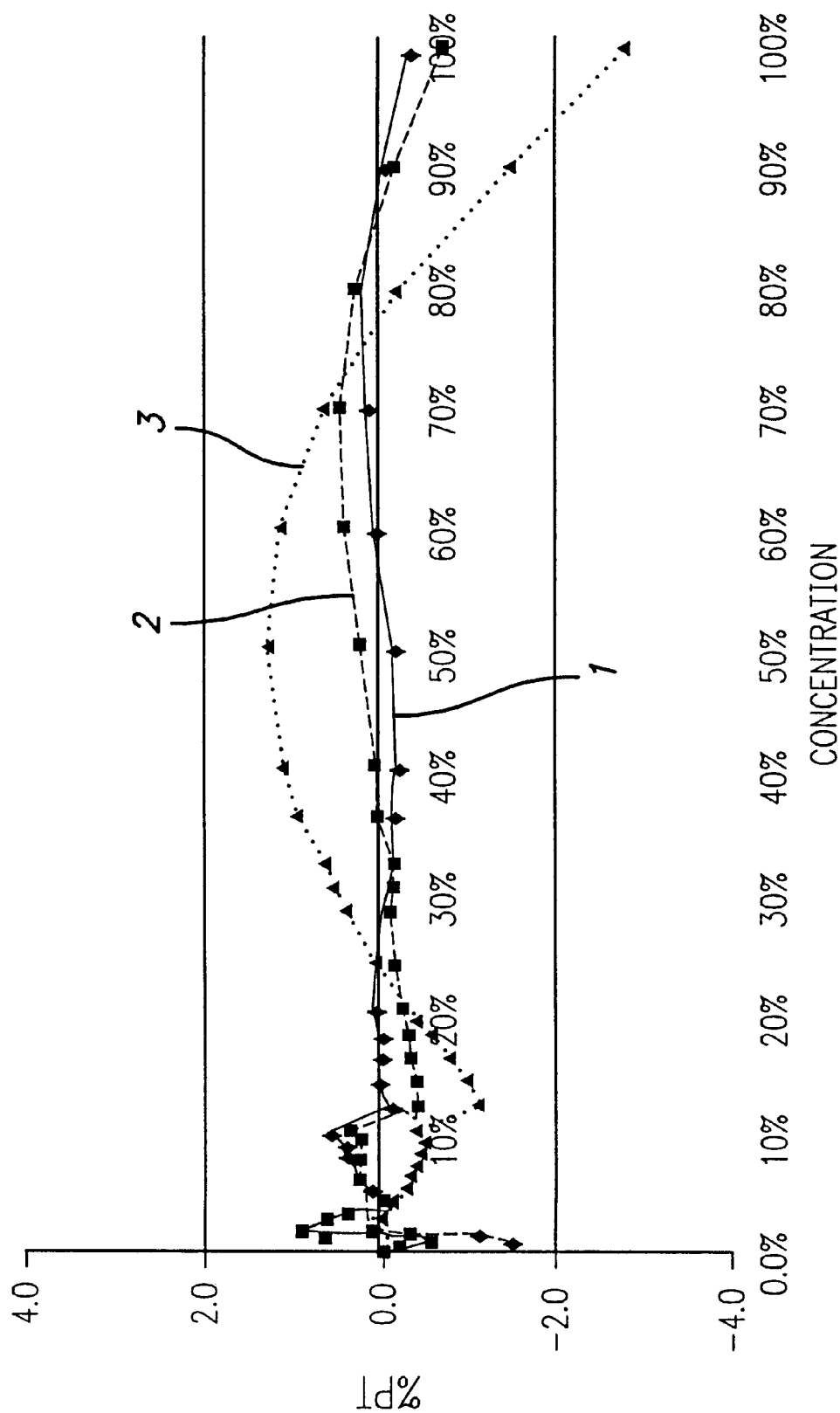
FIG. 1 is a graph illustrating differences in error of a calibration curve caused by weighting operations.
Figure 2:
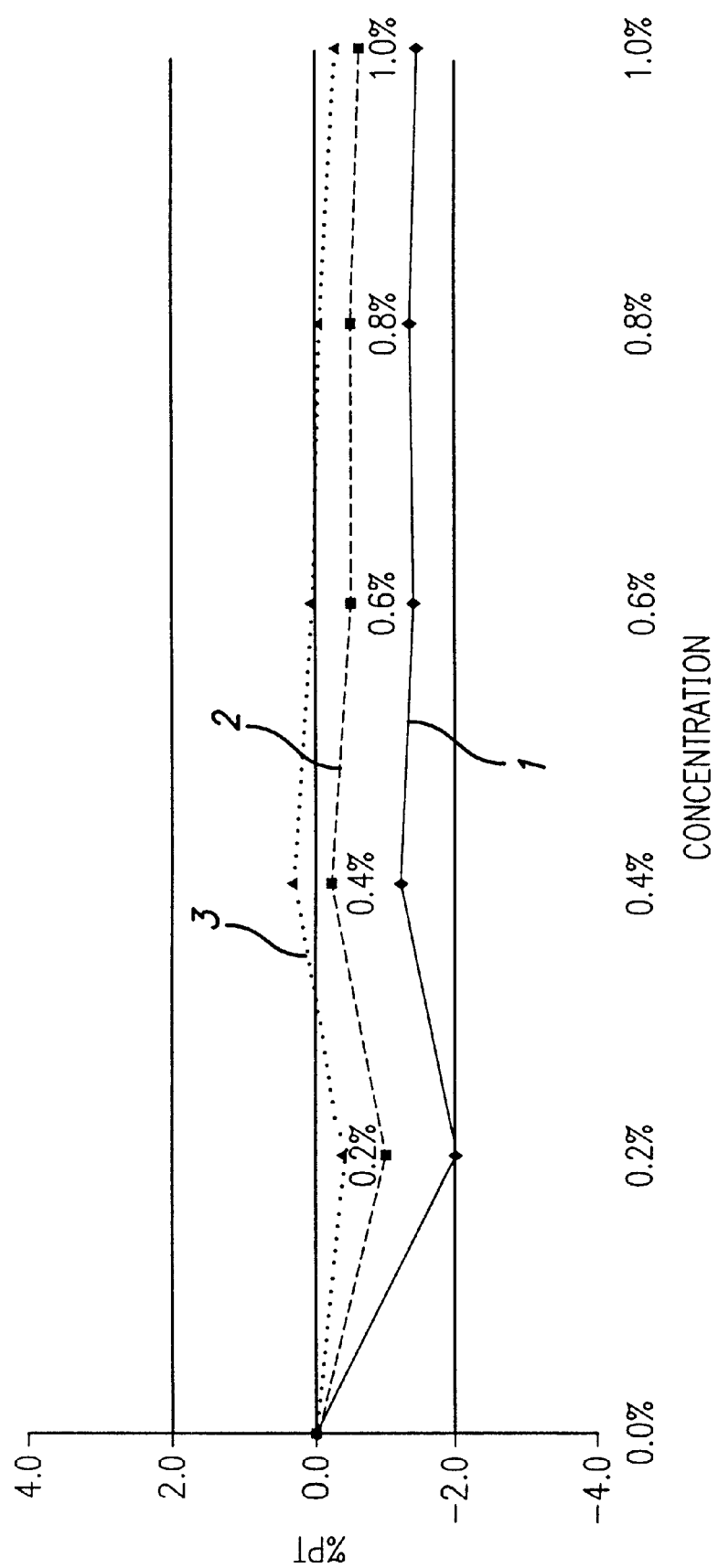
FIG. 2 is an enlarged graph showing a low-concentration area in FIG. 1.
Figure 3:
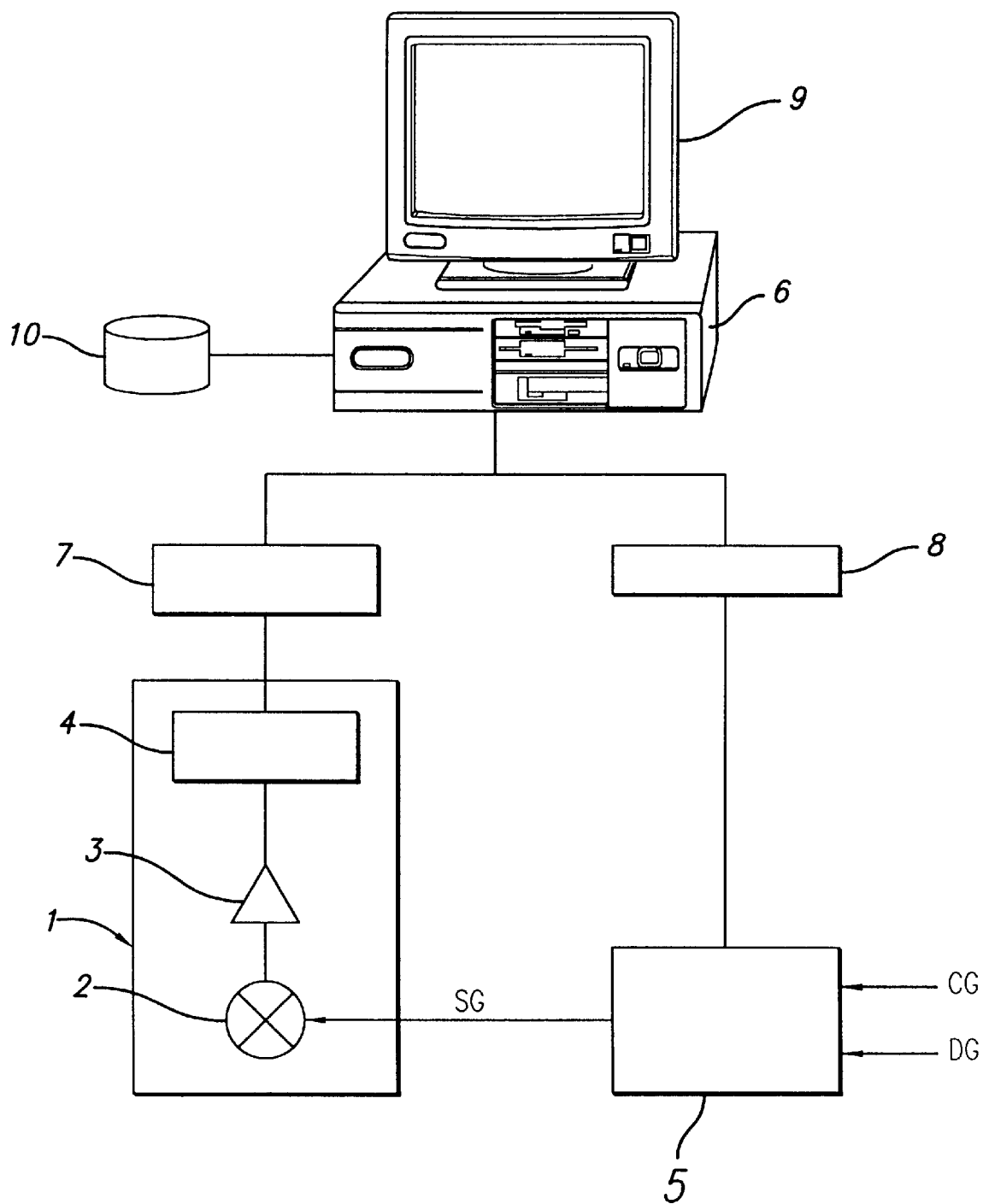
FIG. 3 is a schematic view showing the construction of a conventional device for obtaining a calibration curve.

FIG. 1 shows differences in the error of the calibration curves obtained by the respective weighting operations, and FIG. 2 shows the low-concentration portion of FIG. 1 in an enlarged manner. In both FIGS. 1 and 2, the axis of abscissas represents the concentration (%), and the axis of ordinates represents the size of error (% PT). Here, in these Figures, curves indicated by ① through ③ correspond to the respective weighting operations ① through ③.

The following facts are shown by FIGS. 1 and 2: In the low-concentration area, the error is improved increasingly from ① to ② and then ③. In contrast, in the high-concentration area, the error is improved increasingly from ③ to ② and then ①. This is explained as follows: In the case of method ① using the inverse number of the divided ratio as the weighting operation, the linear area of the low concentration which conforms to the Lambert-Beer's law deviates from the fourth-order-equation calibration curve.

In method ② (using the inverse number of the square of the divided ratio as the weighting operation) and method ③ (using the inverse number of the divided ratio raised to the 3rd power as the weighting operation), the error becomes smaller because the weighting operation in the low-concentration area is larger. However, in method ③, the weighting operation becomes large, which results in causing greater errors in the high-concentration area.

In contrast, in method ②, the error is maintained not more than the standard value (±2.0% PT) in any of the low-concentration and high-concentration areas, making it possible to minimize the system error in a wider range, including the low-concentration and high-concentration areas. In other words, the linearity between the concentration and the output is improved.

As described above, when the calibration line is approximated by using a polynomial, the inverse number of the square of the divided ratio is used at each point of the calibration curve forming data as the weighting operation, so that the measurable range can be expanded; for example, it is possible to carry out desired measurements with high precision in a wide range, such as a range 50 times the lowest range.

In the forming method for the calibration curve of the present invention, upon carrying out the calibration-line approximation by using a polynomial, the inverse number of the square of the divided ratio is used at each point of the calibration curve forming data as the weighting operation; therefore, the system error that inevitably occurs in the measuring principle in the infrared gas analyzer can be minimized as much as possible. Therefore, it becomes possible to obtain an infrared gas analyzer which can carry out measurements with high precision in a wider range, including the low-concentration and high concentration areas.

What is claimed is:

1. A method for forming a calibration curve in an infrared gas analyzer, the infrared gas analyzer:

being supplied with gases having different concentrations, having outputs corresponding to the concentrations of the gases, sampling the gases as a plurality of at least four points, measuring concentrations of the sampled gases, and approximating a calibration curve with a fourth-order polynomial based upon the measured concentrations, said method comprising the steps of:

computing a weighted coefficient equal to an inverse of the square of a divided ratio of the measured concentrations; and multiplying said calibration curve by said weighted coefficient at each measured concentration.

* * * * *